(12) United States Patent
Flatt et al.

(10) Patent No.: US 9,062,125 B2
(45) Date of Patent: Jun. 23, 2015

(54) USE OF GIP FOR THE TREATMENT OF DISORDERS ASSOCIATED WITH DYSFUNCTIONAL SYNAPTIC TRANSMISSION

(75) Inventors: Peter Raymond Flatt, Portrush (GB); Christian Holscher, Coleraine (GB); Victor Alan Gault, Ballymoney (GB)

(73) Assignee: Innovation Ulster Limited, Coleraine (GB)

( * ) Notice: Subject to any disclaimer, the term of this patent is extended or adjusted under 35 U.S.C. 154(b) by 0 days.

(21) Appl. No.: 12/676,991

(22) PCT Filed: Sep. 8, 2008

(86) PCT No.: PCT/EP2008/007337
§ 371 (c)(1),
(2), (4) Date: Mar. 8, 2010

(87) PCT Pub. No.: WO2009/030498
PCT Pub. Date: Mar. 12, 2009

(65) Prior Publication Data
US 2010/0204106 A1 Aug. 12, 2010

(30) Foreign Application Priority Data
Sep. 7, 2007 (GB) .................................. 0717388.3

(51) Int. Cl.
*A01K 31/00* (2006.01)
*A61K 38/00* (2006.01)
*C07K 14/645* (2006.01)

(52) U.S. Cl.
CPC ............... *C07K 14/645* (2013.01); *A61K 38/00* (2013.01)

(58) Field of Classification Search
None
See application file for complete search history.

(56) References Cited

FOREIGN PATENT DOCUMENTS

WO WO 03/011892 A2 2/2003
WO WO 2007/028632 A2 3/2007

OTHER PUBLICATIONS

Nyberg et al. "Immunohistochemical Distribution of Glucose-Dependent Insulinotropic Polypeptide in the Adult Rat Brain" Journal of Neuroscience Research 2007 vol. 85: 2099-2119.
Hietala et al. "Glucose-Dependent Insulinotropic Polypeptide Induces Progenitor Cell Proliferation in Adult Hippocampus" Journal of Neurological Sciences Poster Abstracts Nov. 2005 XP009111974 vol. 238(No. suppl. 1): S344-S345.
Klyubin et al. "Amyloid β Protein Immunotherapy Neutralizes Aβ Oligomers that Disrupt Synaptic Plasticity in vivo" Nature Medicine 2005 11(5):556-561.
Walsh et al. "Naturally Secreted Oligomers of Amyloid β Protein Potently Inhibit Hippocampal Long-term Potentiation in vivo" Nature 2002 416:535-539.

*Primary Examiner* — Olga N Chernyshev
(74) *Attorney, Agent, or Firm* — Licata & Tyrrell P.C.

(57) ABSTRACT

The present invention relates to a peptide comprising at least 12 amino acid residues from the N-terminal end of gastric inhibitory polypeptide, or an analog thereof, which are useful to prophylactically prevent, improve, or reverse the diminished cognitive function associated with these types of disorders, by increasing (or sustaining) the LTP of synaptic transmission. Moreover, sustaining LTP may find utility in the prophylaxis of neurological disease by delaying the onset of impaired cognitive processes, and could serve as a treatment, not only for the diminished cognitive function caused by neurodegeneration, but also for the dysfunctional cognitive processes associated with trauma or age. Additionally, the peptides and analogs of the present invention find are useful to improve the altered cognitive function associated with hyperexcitability-type disorders, by reducing the elevated level of LTP of synaptic transmission.

5 Claims, 10 Drawing Sheets

SEQ ID NO: 1

YAEGTFISDYSIAMDKIHQQDFVNWLLAQKGKKNDWKHNITQ

SEQ ID NO: 2

YAPGTFISDYSIAMDKIHQQDFVNWLLAQKGKKNDWKHNITQ

SEQ ID NO: 3

AAEGTFISDYSIAMDKIHQQDFVNWLLAQKGKKNDWKHNITQ

SEQ ID NO: 4

YAEGTFISDYSIAMDKIHQQDFVNWLLAQKGKKNDWKHNITQ

USE OF GIP FOR THE TREATMENT OF DISORDERS ASSOCIATED WITH DYSFUNCTIONAL SYNAPTIC TRANSMISSION

This application is the U.S. National Phase of PCT/EP2008/007337 filed Sep. 8, 2008, which claims the benefit of priority of United Kingdom Serial No. 0717388.3 filed Sep. 7, 2007.

BACKGROUND

Gastric inhibitory polypeptide (GIP) is an incretin hormone of the secretin family. It was so named because it was originally shown to inhibit histamine-induced gastric acid secretion from innervated canine Bickel-type pouches. However, subsequent studies to elucidate its wider physiological properties established that physiological concentrations of GIP were capable of stimulating insulin secretion from pancreatic beta cells. Thus, the hormone is also known as "glucose-dependent insulinotropic polypeptide".

Human GIP is a 42 amino acid peptide derived from the processing of a 153 amino acid precursor, whose gene is located on chromosome 17 and spans 10 kb. Incretin hormones are released in response to nutrient ingestion, and act to potentiate the glucose-induced insulin response. GIP is released from intestinal K-cells, and its primary role is to modulate glucose-dependent insulin secretion. GIP can also stimulate proinsulin gene transcription and translation. Furthermore, GIP acts as a beta cell mitogenic factor, enhancing the growth, differentiation and proliferation of pancreatic beta cells. GIP has also been shown to inhibit hepatic glucose production, and to stimulate glucose transport, fatty acid synthesis and lipoprotein lipase activity in adipocytes.

The insulinotropic effect on pancreatic islets, and the glucose-lowering effect in peripheral tissues, makes GIP an attractive candidate as a potential therapeutic agent for the treatment of diabetes, obesity and related metabolic disorders.

Neuroplasticity is a process that involves the continual formation of new neural connections, which occurs during the (re-)organisation of the brain in response to activity and experience. Activity-dependent synaptic plasticity plays a vital role in sculpting synaptic connections during development. However, although well known to occur during development, the process is also a central feature of the adult brain. The plastic nature of neuronal connections allows the brain to continually develop in response to experience, and to circumvent the impaired neuronal signalling that occurs as a consequence of trauma or damage to neurons.

There are two types of modifications that are thought to occur in the brain during this process: 1) morphological changes to the neurons themselves, specifically in the area of the synapse; and 2) an increase in the number of synapses between neurons. The efficiency of synaptic signalling is often dependent on either (or both) of these modifications. Indeed, it is widely accepted that processes such as memory formation and learning ability are dependent on alterations in synaptic efficiency that permit strengthening of associations between neurons. Moreover, synaptic plasticity at certain synapses is thought to be both necessary and sufficient for the process of storing information in the brain.

Long-term potentiation (LTP) has long been proposed as a model for the mechanism by which the strengthening of synaptic connections can be achieved. It has been widely demonstrated that high-frequency stimulation can cause a sustained increase in efficiency of synaptic transmission. Based on this finding, it is believed that the synaptic changes that underpin at least certain forms of learning and memory are similar to those changes required for expression of LTP.

Furthermore, it is widely accepted that impaired LTP is often associated with impaired cognitive function. In this regard, for a number of years now, studies have reported cognitive deficits in aged rats. In particular, aged rats have been shown to exhibit deficits in spatial information processing. Correlated with deficits in performance in spatial learning, was a deficit in LTP in the CA1 region of the rodent brain; wherein severely impaired animals did not sustain LTP, whilst sustained LTP was observed in those animals that were relatively unimpaired in spatial learning.

Therefore, cognitive deficits are a hallmark of a number of neurological disorders. For example, the symptoms of age-related memory impairment are often similar to those symptoms associated with the early stages of neurodegenerative diseases such as Alzheimer's disease. Clearly, a major goal in the field of neuroscience is to sustain LTP in circumstances where LTP is impaired, either by age, disease-associated causes, or by any other instance resulting in impaired synaptic transmission.

However, there is growing evidence that mature neurons may also possess mechanisms to prevent the strengthening of input synapses. Such homeostatic regulation ensures that a neuron operates within an optimal activity range, a process that is integral to maintaining the highly plastic nature of the brain. This is evident in the hippocampus, where pyramidal cells of the CA1 region each receive thousands of excitatory inputs with the potential for activity-dependent enhancement of synaptic transmission. In the absence of a mechanism to limit synaptic strengthening, the physiological balance can be compromised, resulting in the LTP process being shut down, and ultimately leading to a reduced capacity of the entire neuronal circuit for storing information. Therefore, the process of depotentiation also acts as a critical mediator in regulating neuronal homeostasis and ensuring the coordinated control of the strength of synaptic transmission. Depotentiation is now thought to play a role in the removal of redundant information from the memory. As such, depotentiation could act as a potential therapeutic measure in disorders associated with overactive cognitive processes.

It is an object of the present invention to prophylactically prevent, improve, or reverse the diminished cognitive function associated with these types of disorders, by increasing (or sustaining) the LTP of synaptic transmission. Moreover, sustaining LTP may find utility in the prophylaxis of neurological disease by delaying the onset of impaired cognitive processes, and could serve as a treatment, not only for the diminished cognitive function caused by neurodegeneration, but also for the dysfunctional cognitive processes associated with trauma or age. Additionally, it is an object of the present invention to improve the altered cognitive function associated with hyperexcitability-type disorders, by reducing the elevated level of LTP of synaptic transmission.

SUMMARY OF THE INVENTION

According to a first aspect of the present invention, there is provided use of a peptide comprising at least 12 amino acid residues from the N-terminal end of gastric inhibitory polypeptide, or an analogue thereof, for the treatment and prophylaxis of neurological disorders caused by, or associated with, dysfunction of long-term potentiation of synaptic transmission.

According to a second aspect of the present invention, there is provided use of a peptide comprising at least 12 amino acid residues from the N-terminal end of gastric inhibitory polypeptide, or an analogue thereof, for the manufacture of a medicament for the treatment and prophylaxis of neurological disorders caused by, or associated with, dysfunction of long-term potentiation of synaptic transmission.

According to a further aspect of the present invention, there is provided a method of treating neurological disorders caused by, or associated with, dysfunction of long-term potentiation of synaptic transmission; wherein the method comprises the administration of a pharmaceutically acceptable amount of a peptide comprising at least 12 amino acid residues from the N-terminal end of gastric inhibitory polypeptide, or an analogue thereof, to a subject suffering from a neurological disorder caused by, or associated with, dysfunctional long-term potentiation of synaptic transmission.

By the term "dysfunction" is meant any disturbance resulting in the abnormal functioning of a process, whereby the process no longer follows a conventional functional pattern. The abnormal functioning of the process involves: impaired LTP, the treatment comprising enhancement; and enhanced LTP, the treatment comprising impairment.

Human GIP comprises a polypeptide with an amino acid sequence as shown in SEQ ID NO: 1. The peptide useful in the present invention comprises at least 12 amino acid residues from the N-terminal end of gastric inhibitory polypeptide. Optionally, the peptide is GIP(1-12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42). Alternatively, the peptide analogue is an analogue of GIP(1-12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42).

Optionally, the gastric inhibitory polypeptide is human GIP.

The peptide is optionally an analogue of GIP(1-12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42).

Optionally, the peptide analogue comprises at least 12 amino acid residues from the N-terminal end of gastric inhibitory polypeptide and further comprises one or more amino acid substitutions or modifications selected from the group consisting of: an amino acid substitution or modification at position 1; an amino acid substitution or modification at position 2; an amino acid substitution or modification at position 3; modification by attachment of a polymer moiety of the general formula HO—(CH$_2$—O—CH$_2$)$_n$—H; and modification by acyl radical addition, with the proviso that the analogue is not Tyr(1) glucitol GIP(1-42).

The amino acid modification at position 1 is not N-terminal glycation of GIP(1-42). Optionally, when the peptide analogue comprises 12-41 amino acid residues from the N-terminal end of gastric inhibitory polypeptide, the peptide is not Tyr(1) glucitol GIP(1-12, 13, 14, 15, 16, 17, 18, 19, 20, 21, 22, 23, 24, 25, 26, 27, 28, 29, 30, 31, 32, 33, 34, 35, 36, 37, 38, 39, 40, or 41). Optionally, when the peptide analogue comprises 12-42 amino acid residues from the N-terminal end of gastric inhibitory polypeptide, the amino acid modification at position 1 is not N-terminal glycation. Optionally, when the peptide analogue comprises 12-41 amino acid residues from the N-terminal end of gastric inhibitory polypeptide, the peptide analogue is not Tyr(1) glucitol GIP(1-12, 13, 14, 15, 16, 17, 18, 19, 20, 21, 22, 23, 24, 25, 26, 27, 28, 29, 30, 31, 32, 33, 34, 35, 36, 37, 38, 39, 40, or 41). Optionally, when the peptide analogue comprises 12-42 amino acid residues from the N-terminal end of gastric inhibitory polypeptide, the amino acid modification at position 1 is not N-terminal glycation.

Preferably, the peptide analogue is resistant to degradation by dipeptidyl peptidase IV (DPP IV).

Optionally, the peptide analogue further comprises at least one amino acid modification, said at least one amino acid modification comprising the attachment of a polymer moiety of the general formula HO—(CH$_2$—O—CH$_2$)$_n$—H, in which n is an integer between 1 and about 22.

Optionally, the polymer moiety has an average molecular weight of no more than 1000 Da. Preferably, the polymer moiety has an average molecular weight of less than 1000 Da.

Preferably, n is an integer between 1 and about 10. More preferably, n is an integer between about 2 and about 5.

Optionally, the polymer moiety has a branched structure. The branched structure may comprise the attachment of at least two polymer moieties of linear structure. Alternatively, the branch point may be located within the structure of each polymer moiety. Alternatively, the polymer moiety has a linear structure.

Some or all monomers of the polymer moiety can be associated with water molecules. Attachment of the polymer moiety can be achieved via a covalent bond. Optionally, the covalent bond is a stable covalent bond. Alternatively, the covalent bond is reversible. The covalent bond can be hydrolysable.

The or each polymer moiety can be attached adjacent the N-terminal amino acid of the peptide analogue; adjacent the C-terminal amino acid of the peptide analogue; or to a naturally occurring amino acid selected from the group including, but not limited to, lysine, cysteine, histidine, arginine, aspartic acid, glutamic acid, serine, threonine, and tyrosine. Alternatively, the peptide analogue further comprises substitution of a naturally occurring amino acid with an amino acid selected from the group including, but not limited to, lysine, cysteine, histidine, arginine, aspartic acid, glutamic acid, serine, threonine, and tyrosine; the or each polymer moiety being attached to the or each substituted amino acid. Optionally, the or each polymer moiety is attached adjacent the C-terminal amino acid. Further optionally, the or each polymer moiety is attached to the C-terminal amino acid.

Optionally, the or each polymer moiety is attached to a lysine residue. The or each polymer moiety can be attached to the alpha or epsilon amino groups of lysine. The lysine residue can be chosen from the group consisting of Lys(16), Lys(30), Lys(32), Lys(33), and Lys(37).

As used throughout, the term "mini-PEG" (or "mPEG") is intended to be synonymous with an attached polymer of polyethylene glycol as previously described herein in which n is an integer between 1 and about 22.

Optionally, the peptide analogue further comprises a modification by acyl radical addition, optionally a fatty acid addition, at an epsilon amino group of an amino acid residue.

Optionally, the peptide analogue further comprises a modification by acyl radical addition, optionally a fatty acid addition, at an epsilon amino group of at least one lysine residue. Further optionally, the lysine residue may be chosen from the group consisting of Lys(16), Lys(30), Lys(32), Lys(33), and Lys(37). Alternatively, the peptide analogue further comprises substitution of a naturally occurring amino acid with an amino acid selected from the group including, but not limited to, lysine, cysteine, histidine, arginine, aspartic acid, glutamic acid, serine, threonine, and tyrosine; the or each modification by acyl radical addition being attached to the or each substituted amino acid.

Optionally, the modification comprises the addition of a fatty acid selected from the group comprising, but not limited to, a C-8 octanoyl group, a C-10 decanoyl group, a C-12 lauroyl group, a C-14 myristoyl group, a C-16 palmitoyl group, a C-18 stearoyl group, or a C-20 acyl group Optionally, the fatty acid is a saturated fatty acid. Further optionally, the fatty acid is myristic acid. Preferably, the peptide analogue is Lys(37)Myristic Acid]GIP. Optionally, the peptide analogue enhances LTP of synaptic transmission and is described hereinafter as a peptide analogue agonist. Optionally, the peptide agonist comprises GIP(1-12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42). Optionally, the peptide analogue agonist comprises:
 (a) N-terminal glycation and an amino acid substitution at position 2;
 (b) amino acid modification at position 1, and amino acid substitution at position 2;
 (c) amino acid modification at position 1, or amino acid substitution at position 2, with the proviso that the analogue is not Tyr(1) glucitol GIP(1-42), wherein the amino acid substitution or modification is selected from the group consisting of:
  (i) glycation at position 1;
  (ii) alkylation at position 1;
  (iii) acetylation at position 1;
  (iv) acylation at position 1;
  (v) the addition of an isopropyl group at position 1;
  (vi) the addition of a pyroglutamic acid at position 1;
  (vii) substitution at position 2 by an L-amino acid;
  (viii) substitution at position 2 by amino isobutyric acid or sarcosine;
  (ix) substitution at position 2 by a D-amino acid such as D-Ala(2)GIP;
  (x) conversion of the Ala(2)-Glu(3) bond to a ψ[CH$_2$NH] bond;
  (xi) conversion of the Ala(2)-Glu(3) bond to a stable isostere bond; and
  (xii) substitution at position 2 by beta-alanine, an omega-amino acid, 3-amino propionic acid, 4-amino butyric acid, ornithine, citrulline, homoarginine, t-butylalanine, t-butylglycine, N-methylisoleucine, phenylglycine, and cyclohexylalanine, norleucine, cysteic acid, and methionine sulfoxide;
 (d) amino acid modification comprising the attachment of a polymer moiety of the general formula HO—(CH$_2$—O—CH$_2$)$_n$—H; and
 (e) modification by acyl radical addition, optionally a fatty acid addition, at an epsilon amino group of an amino acid residue.

Optionally, when there is an amino acid substitution at position 2 and an amino acid modification at position 1, each amino acid substitution and/or modification is selected from the group consisting of
  (i.) glycation at position 1;
  (ii.) alkylation at position 1;
  (iii.) acetylation at position 1;
  (iv.) acylation at position 1;
  (v.) the addition of an isopropyl group at position 1;
  (vi.) the addition of a pyroglutamic acid at position 1;
  (vii.) substitution at position 2 by a D-amino acid;
  (viii.) substitution at position 2 by an L-amino acid;
  (ix.) substitution at position 2 by amino isobutyric acid or sarcosine;
  (x.) conversion of the Ala(2)-Glu(3) bond to a ψ[CH$_2$NH] bond;
  (xi.) conversion of the Ala(2)-Glu(3) bond to a stable isostere bond; and
  (xii.) substitution at position 2 by beta-alanine, an omega-amino acid, 3-amino propionic acid, 4-amino butyric acid, ornithine, citrulline, homoarginine, t-butylalanine, t-butylglycine, N-methylisoleucine, phenylglycine, cyclohexylalanine, norleucine, cysteic acid, and methionine sulfoxide.

Optionally, the peptide analogue may further comprise either amino acid modification comprising the attachment of a polymer moiety of the general formula HO—(CH$_2$—O—CH$_2$)$_n$—H; or modification by acyl radical addition, optionally a fatty acid addition, at an epsilon amino group of an amino acid residue; or amino acid modification comprising the attachment of a polymer moiety of the general formula HO—(CH$_2$—O—CH$_2$)$_n$—H and modification by acyl radical addition, optionally a fatty acid addition, at an epsilon amino group of an amino acid residue.

Preferably, the peptide analogue agonist comprises an amino acid modification at position 1, wherein the amino acid modification is an acylation such as, but not limited to, an acetylation. More preferably, the peptide analogue is acylated (optionally acetylated) adjacent the N-terminus. Most preferably, the peptide analogue is acylated (optionally acetylated) at the N-terminal alpha-amine. Optionally, the peptide analogue agonist comprises an amino acid modification at position 1, wherein the amino acid modification is glycation.

Optionally, the peptide analogue agonist comprises an N-alkylated amino acid at position 1. Further optionally, the peptide analogue comprises the addition of an N-terminal isopropyl group at position 1. Further optionally, the peptide analogue comprises the addition of an N-terminal pyroglutamic acid at position 1. Further optionally, the peptide analogue further comprises a modification by fatty acid addition at an epsilon amino group of at least one lysine residue, and an amino acid substitution or modification at one or both of positions 1, and 2.

Optionally, the peptide analogue agonist comprises one or more of the following amino acid substitutions: substitution at position 2 by proline, lysine, serine, glycine, a D-amino acid, 4-amino butyric acid (Abu), amino isobutyric acid (Aib), or sarcosine.

Optionally, the peptide agonist is GIP or a fragment thereof, and enhances LTP of synaptic transmission.

Optionally, the peptide agonist and/or the peptide analogue agonist is selected from GIP, [N-Acetylated]GIP, [mPEGylated]GIP, D-Ala(2)GIP, and [Lys(37)Myristic Acid]GIP.

Alternatively, the peptide analogue attenuates LTP of synaptic transmission and is described hereinafter as a peptide analogue antagonist. Optionally, the peptide analogue antagonist comprises:
 (a) an amino acid substitution at one of positions 1 and 3;
 (b) amino acid substitution at each of positions 1 and 3; and
 (c) amino acid substitution at one of positions 1 and 3, wherein the amino acid substitution is selected from the group consisting of:
  (i) substitution at position 1 by an L-amino acid;
  (ii) substitution at position 1 by a D-amino acid;
  (iii) substitution at position 3 by an L-amino acid;
  (iv) substitution at position 3 by amino isobutyric acid or sarcosine;
  (v) substitution at position 3 by a D-amino acid;
  (vi) conversion of the Ala(2)-Glu(3) bond to a ψ[CH$_2$NH] bond;
  (vii) conversion of the Ala(2)-Glu(3) bond to a stable isostere bond; and
  (viii) substitution at position 1 or 3 by beta-alanine, an omega-amino acid, 3-amino propionic acid, 4-amino butyric acid, ornithine, citrulline, homoarginine, t-butylalanine, t-butylglycine, N-methylisoleucine, phenylglycine, and cyclohexylalanine, norleucine, cysteic acid, and methionine sulfoxide.

Optionally, when the amino acid substitution is at both of positions 1 and 3, each amino acid substitution is selected from the group consisting of:
(a) substitution at position 1 by a D-amino acid;
(b) substitution at position 1 by an L-amino acid;
(c) substitution at position 3 by a D-amino acid;
(d) substitution at position 3 by an L-amino acid;
(e) substitution at position 1 and/or 3 by amino isobutyric acid or sarcosine;
(f) conversion of the Ala(2)-Glu(3) bond to a ψ[CH$_2$NH] bond;
(g) conversion of the Ala(2)-Glu(3) bond to a stable isostere bond; and
(h) substitution at position 1 and/or 3 by beta-alanine, an omega-amino acid, 3-amino propionic acid, 4-amino butyric acid, ornithine, citrulline, homoarginine, t-butylalanine, t-butylglycine, N-methylisoleucine, phenylglycine, cyclohexylalanine, norleucine, cysteic acid, and methionine sulfoxide.

Optionally, the peptide analogue antagonist comprises one or more of the following amino acid substitutions: substitution at position 1 and/or 3 by proline, lysine, serine, a D-amino acid, or sarcosine.

Optionally, the peptide analogue antagonist is selected from Pro(3)GIP, and Ala(1)GIP.

Optionally, the peptide agonist or the peptide analogue agonist or the peptide analogue antagonist consists of 15 to 30 amino acids from the N-terminal end of GIP(1-42). Alternatively, the peptide agonist or the peptide analogue agonist or antagonist consists of at least 30 amino acids from the N-terminal end of GIP(1-42).

Alternatively or additionally, the peptide analogue agonist or the peptide analogue antagonist further comprises a modification by fatty acid addition at an epsilon amino group of at least one lysine residue. Further optionally, the lysine residue may be chosen from the group consisting of Lys(16), Lys(30), Lys(32), Lys(33), and Lys(37).

Optionally, the modification comprises the addition of a fatty acid selected from the group comprising, but not limited to, a C-8 octanoyl group, a C-10 decanoyl group, a C-12 lauroyl group, a C-14 myristoyl group, a C-16 palmitoyl group, a C-18 stearoyl group, or a C-20 acyl group. Optionally, the fatty acid is a saturated fatty acid. Further optionally, the fatty acid is myristic acid.

Neurological disorders comprise a group of disorders that affect a neural network. The neural network comprises the central nervous system (CNS); the spinal cord; and the peripheral nervous system (PNS).

Preferably, the group of disorders are characterised by dysfunctional electrochemical communication between neurons. The electrochemical communication can comprise chemical communication across a synapse; or electrical communication across a gap junction.

A neurological disorder comprises a disorder selected from the group of disorders affecting cognitive function; and dysfunctional cognitive processes.

Disorders negatively affecting cognitive function include, but are not limited to: dementia, stroke, schizophrenia, bipolar disorder, and neurodegenerative diseases. Disorders positively affecting cognitive function include, but are not limited to: post-traumatic stress disorder, epilepsy, Tourette's syndrome, and hallucinations.

Neurodegenerative diseases are selected from, but not limited to: Alzheimer's disease (AD), Creutzfeldt-Jacob disease (CJD), Huntington's disease, and Parkinson's disease.

Dysfunctional cognitive processes include, but are not limited to: attention, calculation, memory, judgment, insight, learning, and reasoning.

For the purposes of the present specification, it is understood that this invention is not limited to the specific methods, treatment regimens, or particular procedures, which as such may vary. Moreover, the terminology used herein is for the purpose of describing particular embodiments and is not intended to be limiting.

As used throughout, the term "gastric inhibitory peptide" (or "GIP") is intended to be synonymous with full length GIP, and GIP(1-42). Preferably, the term refers to human GIP.

The term "polypeptide" is used herein synonymously with the term peptide.

By the term "subject", is meant an individual. Preferably, the subject is a mammal. More preferably, the subject is a human.

BRIEF DESCRIPTION OF THE DRAWINGS

Embodiments of the invention will now be described, by way of example with reference to the accompanying drawings, in which.

MATERIALS AND METHODS

Surgery and LTP Induction Protocols

Male Wistar rats weighing 220-280 g were anaesthetised with urethane (ethyl carbamate, 1.8 g/kg, i.p.) for the duration of all experiments. The animals had been obtained from Harlan, United Kingdom (UK).

A cannula (22 gauge, 0.7 mm outer diameter, 11 mm in length, Bilaney, Kent, UK) was implanted (1.5 mm anterior to bregma, 0.5 mm lateral to the midline and 3.55 mm ventral) into the left hemisphere for intracerebroventricular (icv) injections. Electrodes (tungsten with Teflon coating, Bilaney, Kent, UK) were implanted unilaterally 3.4 mm posterior and 2.5 mm lateral to the midline, and the stimulating electrode 4.2 mm posterior to bregma and 3.8 mm lateral to the midline. The electrodes were slowly lowered through the cortex and the upper layers of the hippocampus and into the CA1 region until the appearance of a negative deflecting (excitatory postsynaptic potential) EPSP that had a latency of ca. 10 ms. Recordings of EPSPs were made from the stratum radiatum in the CA1 region of the right hippocampal hemisphere in response to stimulation of the Schaffer collateral/commissural pathway.

Field EPSPs were recorded on a computerised stimulating and recording unit (PowerLab, ADI instruments, UK) in which the trigger threshold was adjustable. The triggered unit activated a constant current stimulus isolation unit (Neurolog, UK). The data acquisition system was triggered simultaneously to record all events. Sampling speed was at 20 kHz recording of EPSPs.

The 'strong' high frequency stimulation (HFS) protocol for inducing LTP consisted of 3 trains of 200 stimuli, inter-stimulus interval 5 ms (200 Hz), inter-train interval 2 sec. This standard HFS has been shown to induce maximal LTP under these recording conditions (Hölscher et al., 1997). The 'weak' HFS protocol for inducing LTP consisted of 10 trains of 10 stimuli, inter-stimulus interval 5 ms (200 Hz). The strong HFS was used to test the effects of peptides that impair LTP (beta-amyloid), and the weak HFS was used to test peptides that facilitate LTP. In this form of LTP, the control group is not potentiated at a maximal rate, and LTP can decay slowly over time.

Stimulation intensity was 70% of the maximum EPSP. LTP was measured as a % of baseline EPSP slope recorded over a 30 min period prior to drug injection and 60 min prior to application of HFS. Baseline was recorded for 30 min and averaged. This value was taken as 100% of the EPSP slope and all recoded values were normalised to this baseline value.

All experiments were licensed according to UK Home Office regulations, and the "Principles of laboratory animal care" (NIH publication No. 86-23, revised 1985) were followed.

Peptides

Beta-amyloid(25-35) and other peptides used in this study were synthetised on an Applied Biosystems automated peptides synthesiser (Model 432A) using standard solid-phase Fmoc protocols. Peptides were judged pure by reversed phase HPLC on a Waters Millennium 2010 chromatography system, and peptides were subsequently characterised using matrix-assisted laser desorption/ionisation time of flight (MALDI-TOF) mass spectrometry as described previously (Gengler et al., 2006; Hölscher et al., 2007). Peptides were stored in dry form and dissolved in double distilled water before the experiments. 5 µl of peptide solution was injected icv.

Statistics

Each group consisted of 6 animals. Data were analysed using a repeated measures two-way ANOVA, or a repeated measures three level two-way ANOVA with post-hoc tests to discriminate between groups (PRISM, GraphPad software Inc, USA).

EXAMPLES

The following examples are described herein so as to provide those of ordinary skill in the art with a complete disclosure and description of the invention, and are intended to be purely exemplary of the present invention, and are not intended to limit the scope of the invention.

Example 1

Peptide Sequence

Figure 1:
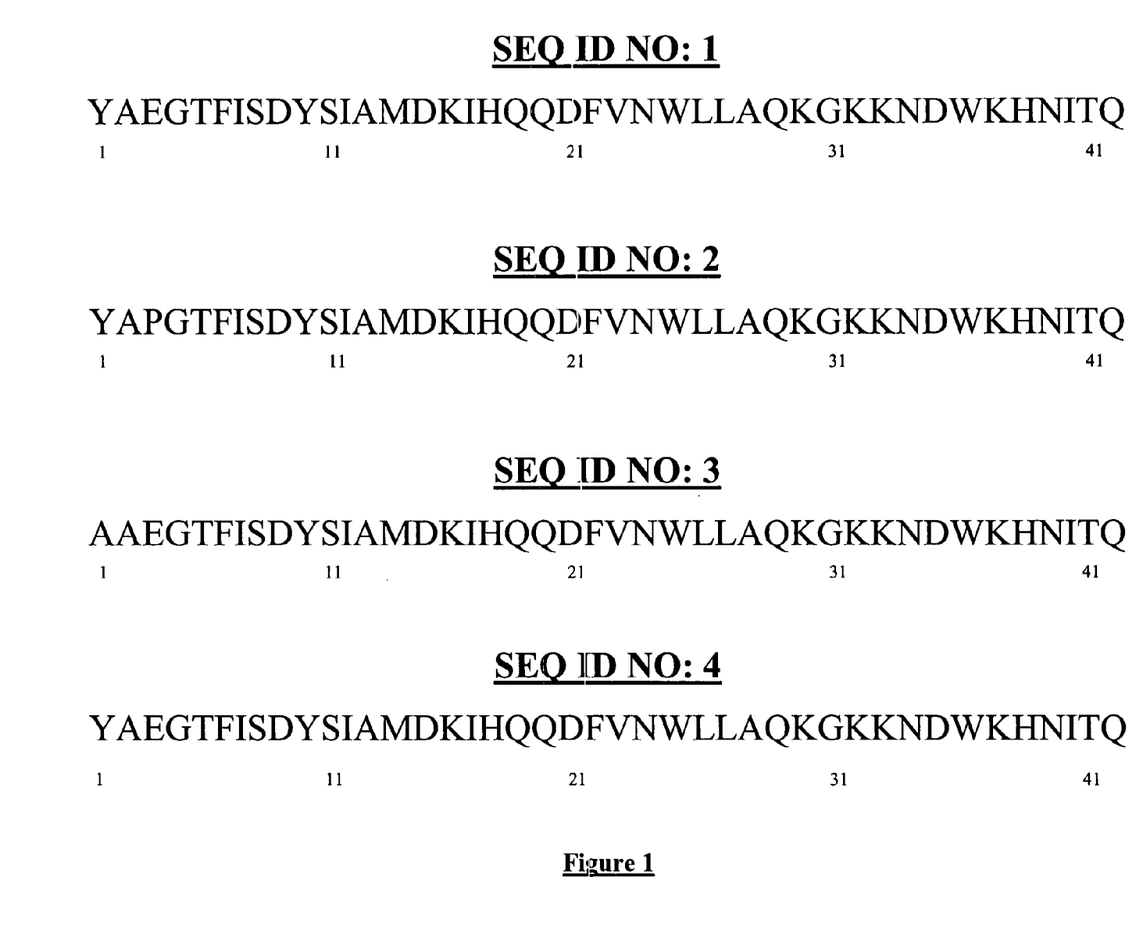
FIG. 1 illustrates the polypeptide sequences of human GIP (1-42) (SEQ ID NO: 1), and peptide analogues of GIP (SEQ ID NOs: 2-4)

The amino acid sequences of human GIP(1-42), and analogues thereof, are given in FIG. 1. The amino acids are numbered below.

SEQ ID NO: 1 illustrates the amino acid sequence of human GIP;
SEQ ID NO: 2 illustrates the amino acid sequence of the analogue Pro(3)GIP;
SEQ ID NO: 3 illustrates the amino acid sequence of the analogue Ala(1)GLP-1; and
SEQ ID NO: 4 illustrates the amino acid sequence of the analogue D-Ala(2)GLP-1.

Example 2

In Vivo Effects of Beta-Amyloid(25-35) Treatment

Figure 2:
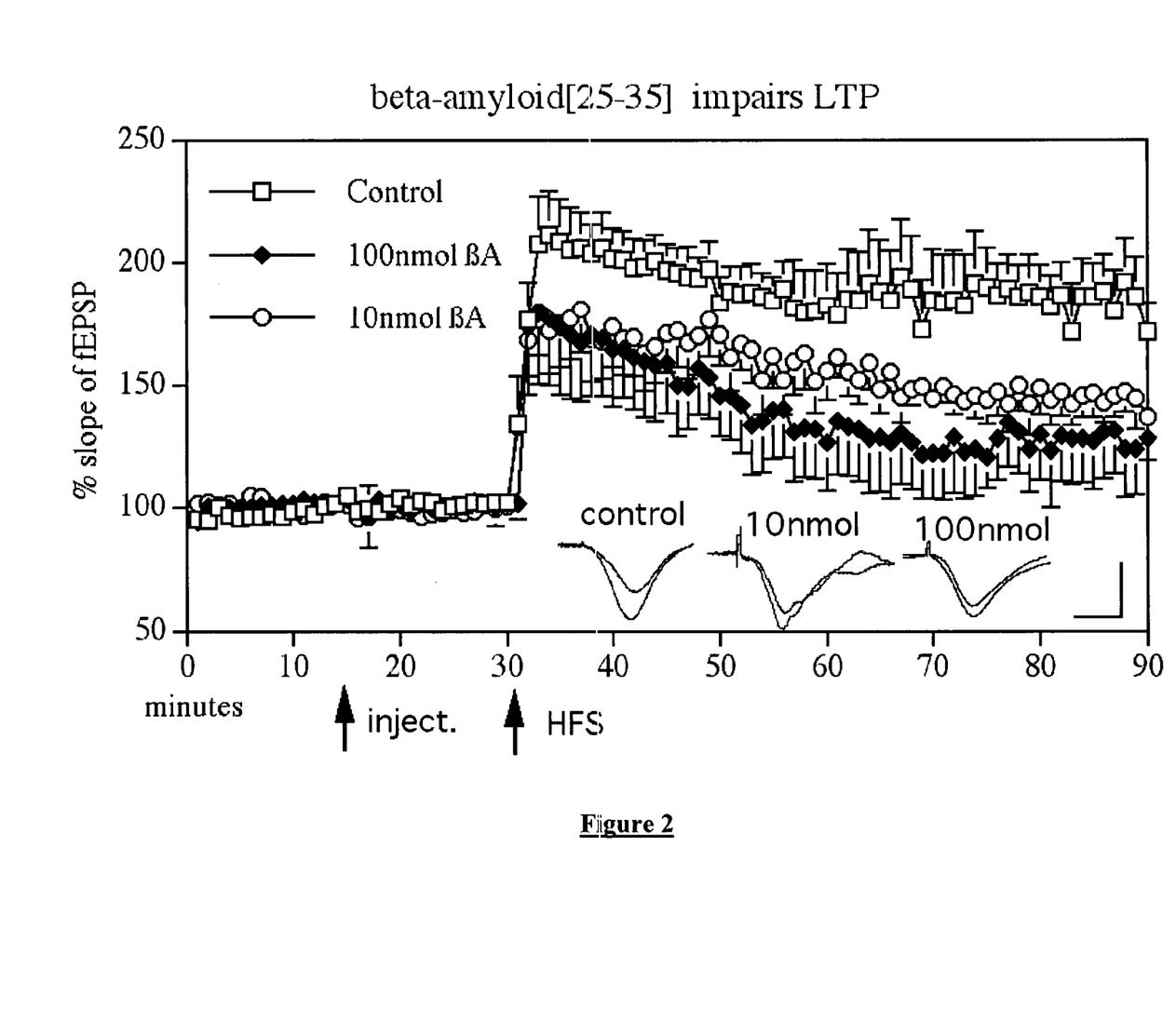
FIG. 2 illustrates the effect of beta-amyloid(25-35) on long-term potentiation of synaptic transmission.

Male Wistar rats were intracerebroventricularly (icv) injected with either vehicle (Control,) 10 nmol (○) or 100 nmol (♦) beta-amyloid (βA)(25-35). LTP was induced 15 min post-injection using the HFS (strong protocol), and the change in EPSP assessed and graphed to represent the change in LTP (FIG. 2). Injection (icv) of 10 nmol βA(25-35) impaired long-term potentiation (LTP) compared with control (two-way ANOVA; p<0.01). Following injection of 100 nmol βA(25-35), LTP development was also impaired (p<0.005). Averaged EPSPs are shown recorded 5 min pre-HFS and 1 h post-HFS. These EPSPs are examples to demonstrate the quality of the recording. As shown, the EPSPs clearly changed after stimulation, and are of high quality with very little noise. Calibration bars are 10 ms horizontal, 1 mV vertical. All groups n=6.

These results demonstrate the detrimental effects of βA(25-35) on LTP.

Example 3

In Vivo Effects of GIP Treatment

Figure 3:
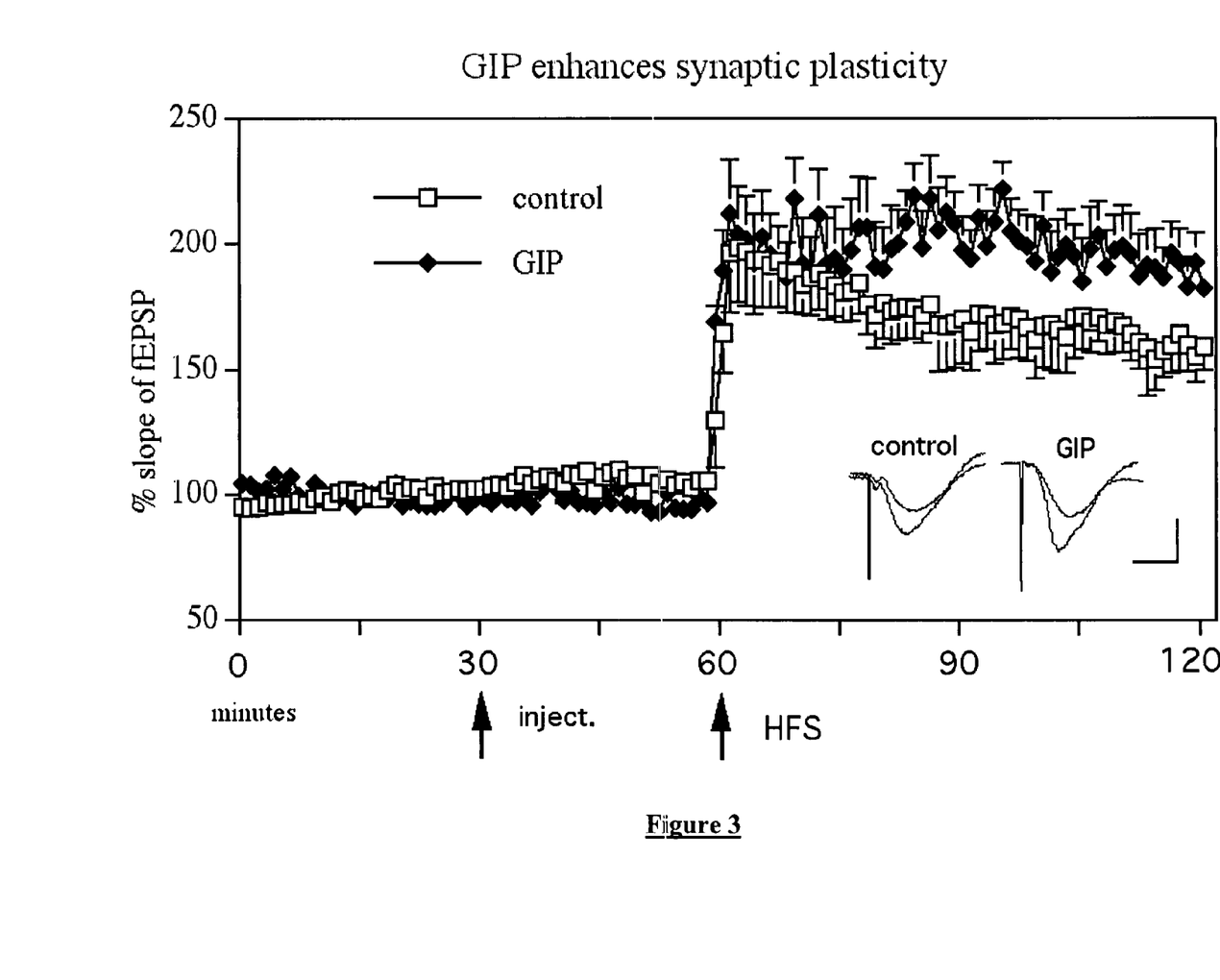
FIG. 3 illustrates the effect of human GIP on long-term potentiation of synaptic transmission.

Male Wistar rats were icv injected with either vehicle (Control,) or 15 nmol human GIP(1-42) (♦). LTP was induced 30 min post-injection using the HFS (weak protocol), and the change in EPSP assessed and graphed to represent the change in LTP (FIG. 3). Injection (icv) of 15 nmol GIP increased long-term potentiation (LTP) compared with control (two-way ANOVA; p<0.01). Interaction between factors was not significant. All groups n=6. Averaged EPSPs are shown recorded 5 min pre-tetanus and 1 h post-tetanus. Calibration bars are 10 ms horizontal, 1 mV vertical.

These results show, for the first time, that human GIP(1-42) has direct and acute modulating effects on synaptic transmission and can enhance the induction of LTP.

Example 4

In Vivo Effect of N-AcGIP Treatment

Figure 4:
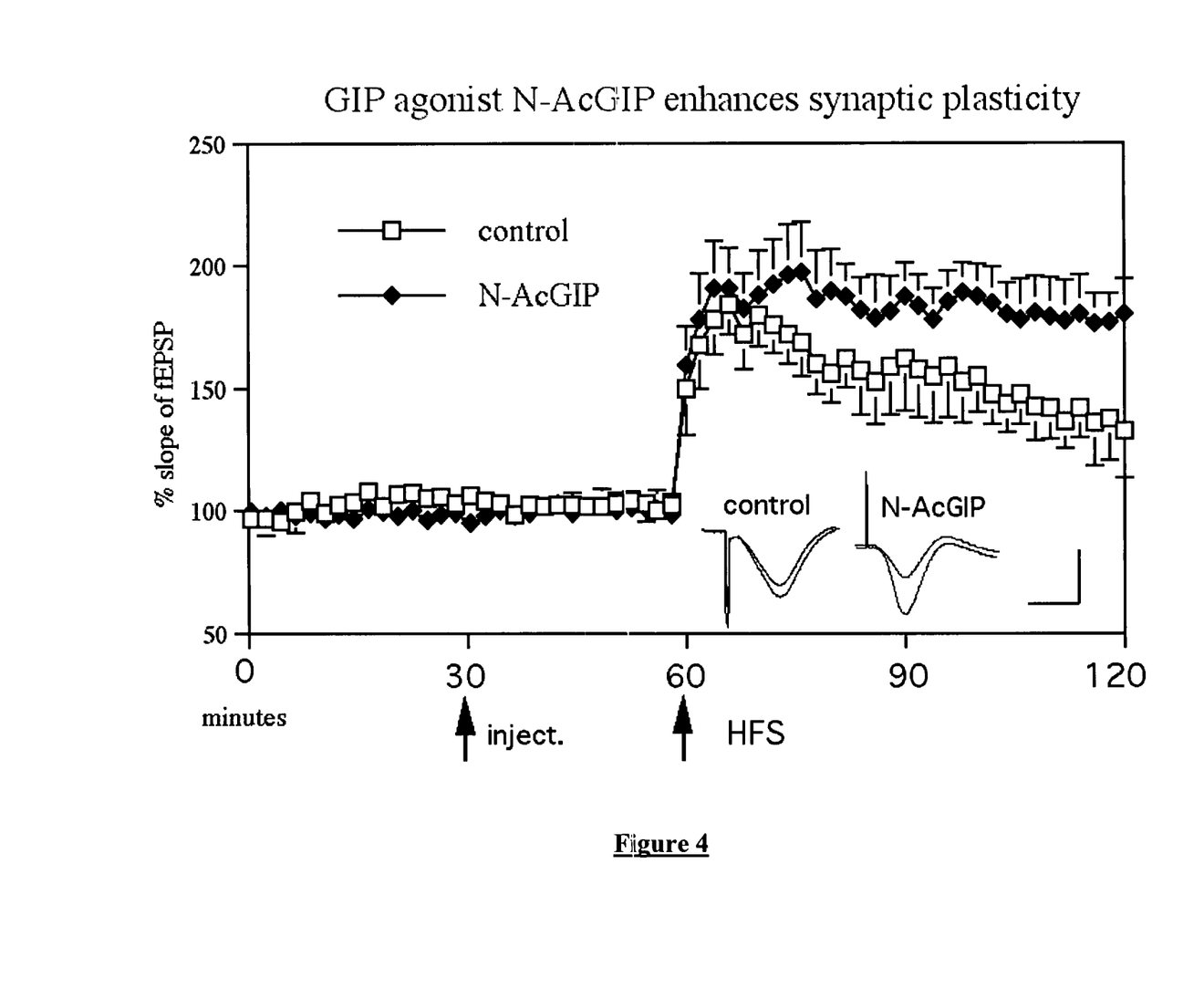
FIG. 4 illustrates the effect of N-AcGIP on long-term potentiation of synaptic transmission.

Here the effect of N-AcGIP (N-terminally acetylated human GIP(1-42)) on its own has been tested on synaptic plasticity. Since N-AcGIP is an agonist, a weak stimulation had to be used to induce sub-maximal long-term potentiation (LTP). If the compound has any facilitating effects, an increase of LTP when compared to control should be observed. Male Wistar rats were icv injected with either vehicle (Control,) or 15 nmol N-AcGIP (♦). LTP was induced 30 min post-injection using the HFS (weak protocol), and the change in EPSP assessed and graphed to represent the change in LTP (FIG. 4). Injection (icv) of 15 nmol N-AcGIP enhanced long-term potentiation (LTP) compared with control (two-way ANOVA; p<0.001). Averaged EPSPs are shown recorded 5 min pre-HFS and 1 h post-HFS. These EPSPs are examples to demonstrate quality of the recording. As shown, the EPSPs clearly changed after stimulation, and are of high quality with very little noise. Calibration bars are 10 ms horizontal, 1 mV vertical. All groups n=6.

These results show, for the first time, that N-AcGIP has direct and acute modulating effects on synaptic transmission and can enhance the induction of LTP.

Example 5

In Vivo Effect of N-AcGIP and Beta-Amyloid(25-35) Treatment

Figure 5:
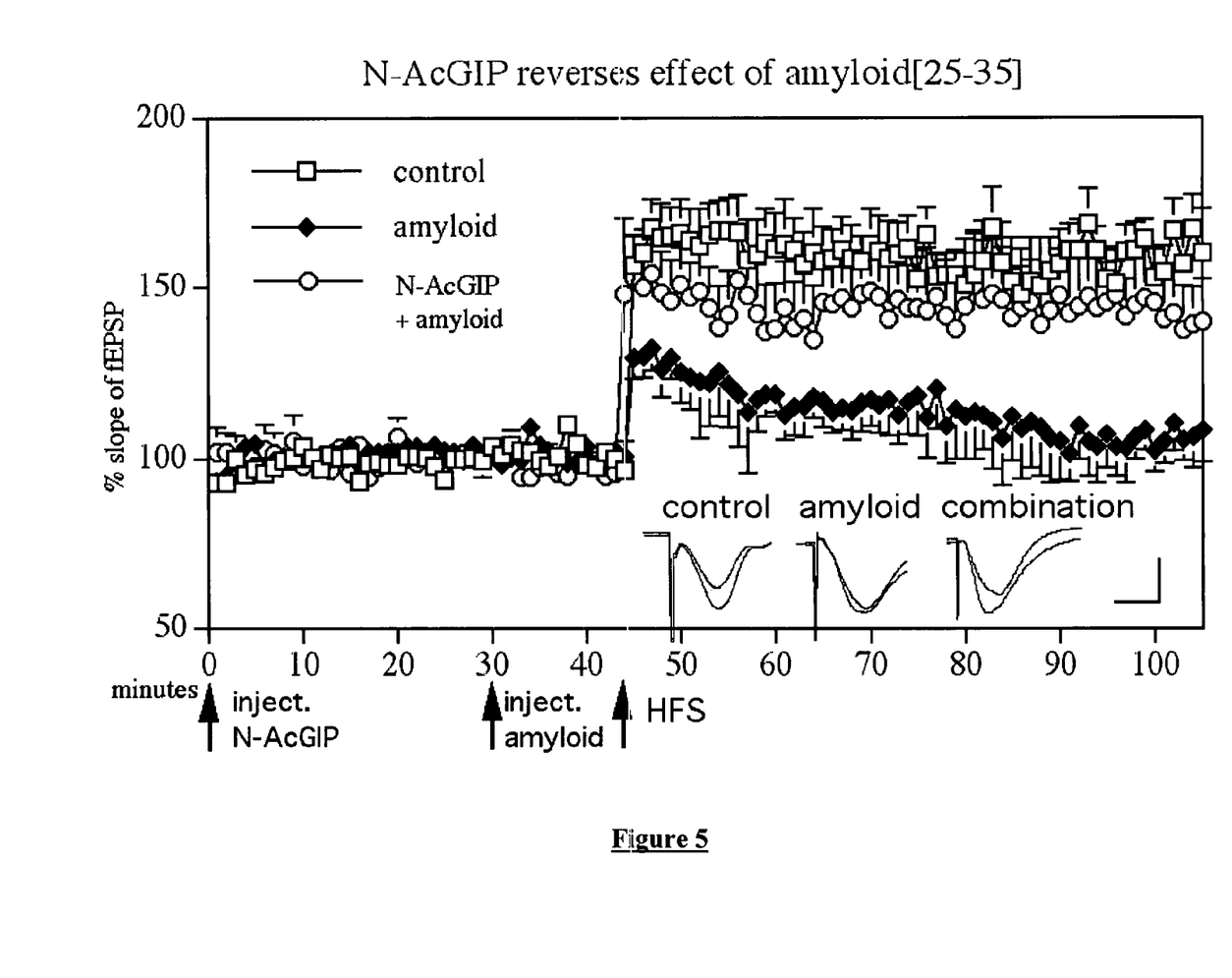
FIG. 5 illustrates the effect of administering N-AcGIP and then beta-amyloid(25-35) on long-term potentiation of synaptic transmission.

Male Wistar rats were icv injected with either vehicle (Control,), 100 nmol βA(25-35) (♦), or a combination of 15 nmol N-AcGIP and 100 nmol βA(25-35) (○). βA(25-35) was injected 30 min after N-AcGIP, and LTP was induced 15 min post-βA(25-35)-injection using the HFS (weak protocol), and the change in EPSP assessed and graphed to represent the change in LTP (FIG. 5). Since this experiment was to test whether N-AcGIP can prevent the βA-induced impairment of LTP, a strong HFS protocol was used to obtain maximal LTP. Therefore, N-AcGIP was not tested on its own in this protocol, since LTP was already induced at maximal level and could not be further enhanced by N-AcGIP (see Example 4 for the effect of N-AcGIP alone). Injection (icv) of 15 nmol N-AcGIP attenuated the βA(25-35)-induced impairment of LTP. A three level ANOVA found an overall difference between groups ($p<0.001$). A two-level two-way ANOVA showed a difference between the βA(25-35) group and control ($p<0.001$). A two-level ANOVA showed a difference between the N-AcGIP group and βA(25-35) combination group and the beta-amyloid group ($p<0.001$). Averaged EPSPs are shown recorded 5 min pre-HFS and 1 h post-HFS. Calibration bars are 10 ms horizontal, 1 mV vertical. All groups n=6.

These results show that N-AcGIP can prevent the βA-induced impairment of LTP.

Example 6

In Vivo Effect of Pro(3)GIP Treatment

Figure 6:
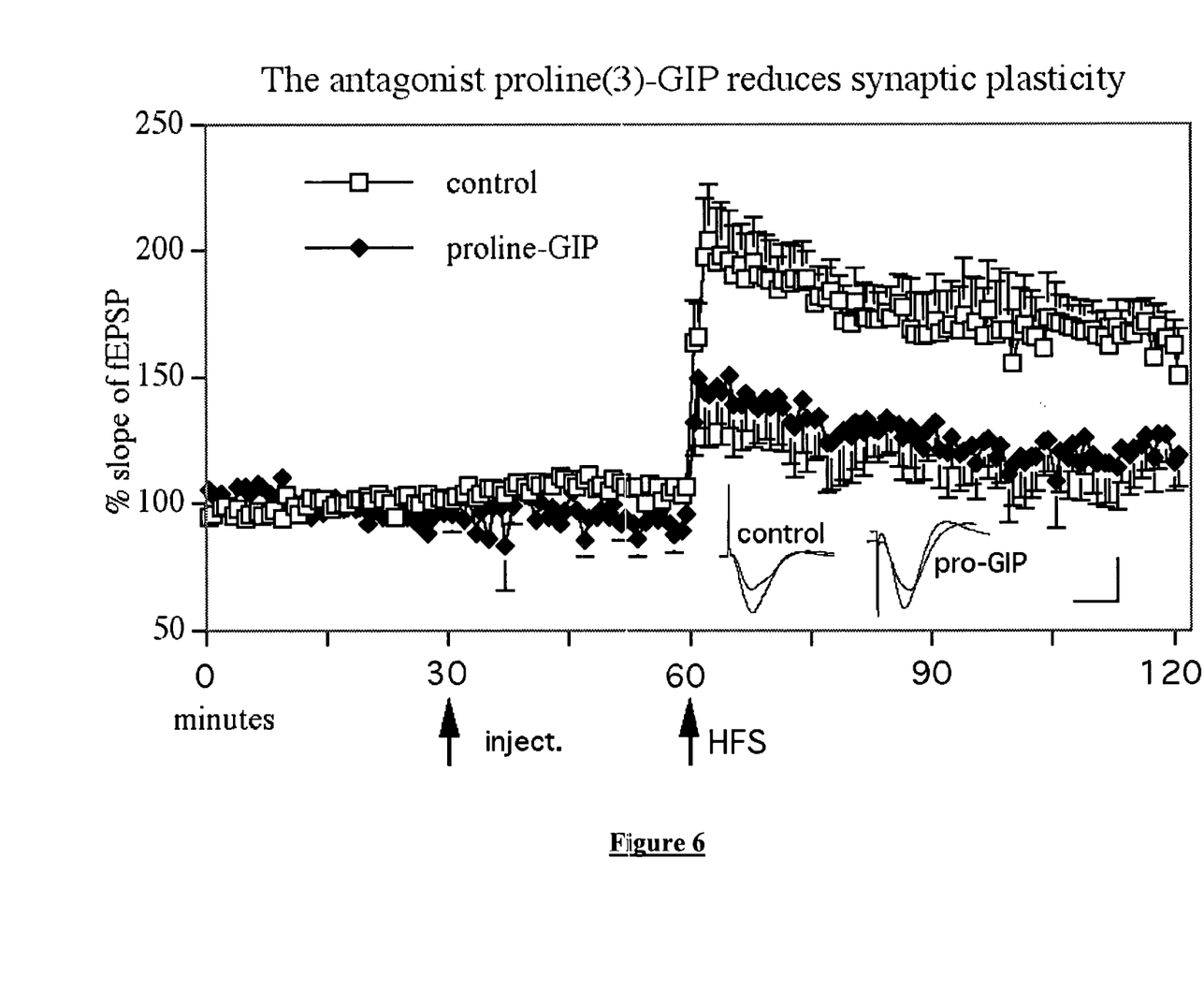
FIG. 6 illustrates the effect of Pro(3)GIP on long-term potentiation of synaptic transmission.

Male Wistar rats were icv injected with either vehicle (Control,) or 15 nmol Pro(3)GIP (♦). Pro(3)GIP is human GIP(1-42) in which Glu at position 3 has been replaced with L-Pro. LTP was induced 30 min post-injection using the HFS (strong protocol), and the change in EPSP assessed and graphed to represent the change in LTP (FIG. 6). Injection (icv) of 15 nmol Pro(3)GIP attenuated long-term potentiation (LTP) compared with control (two-way ANOVA; $p<0.001$). A two-level two-way repeated measures ANOVA showed a difference between the Pro(3)GIP group and control ($DF_{1,10}$; F=21; $p<0.001$) and over time ($DF_{1,119}$; F=1.96; $p<0.005$). Interaction between factors was not significant (see FIG. 2*c*). All groups n=6. Averaged EPSPs are shown recorded 5 min pre-HFS and 1 h post-HFS. Calibration bars are 10 ms horizontal, 1 mV vertical. All groups n=6.

These results show that Pro(3)GIP has direct and acute modulating effects on synaptic transmission and can attenuate the induction of LTP.

Example 7

In Vivo Effects of Treatment with Ala(1)GIP

Figure 7:
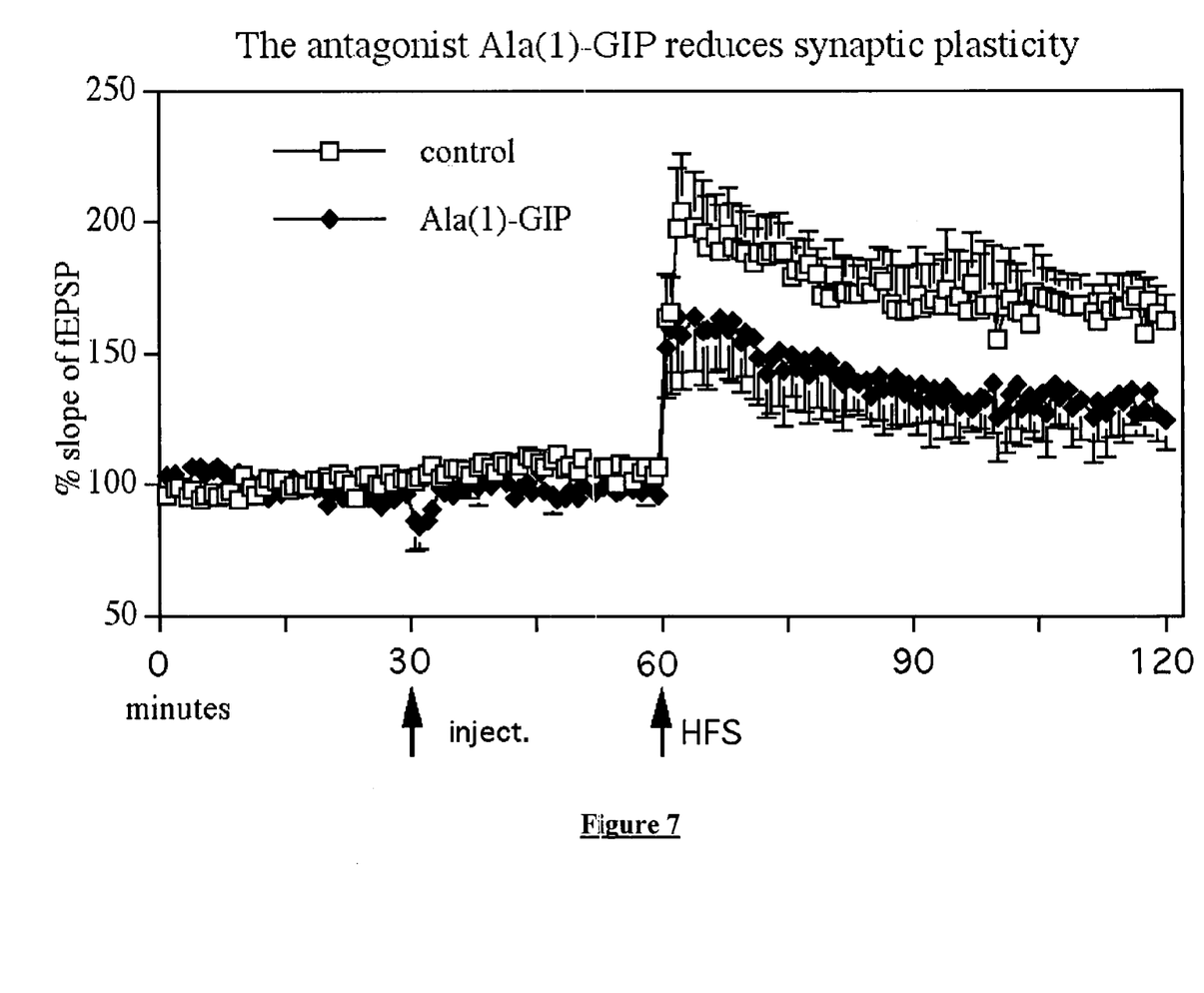
FIG. 7 illustrates the effect of Ala(1)GIP on long-term potentiation of synaptic transmission.

Male Wistar rats were icv injected with either vehicle (Control,) or 15 nmol Ala(1)GIP (♦). Ala(1)GIP is human GIP(1-42) in which Tyr at position 1 has been replaced with L-Ala. LTP was induced 30 min post-injection using the HFS (strong protocol), and the change in EPSP assessed and graphed to represent the change in LTP. Injection (icv) of 15 nmol Ala(1)GIP attenuated long-term potentiation (LTP) compared with control. A two-way repeated measures ANOVA showed a difference between the Ala(1)GIP group and control ($p<0.001$). All groups n=6.

These results show that Ala(1)GIP has direct and acute modulating effects on synaptic transmission and can attenuate the induction of LTP.

Example 8

In Vivo Effects of Treatment with GIP[mPEG]

Figure 8:
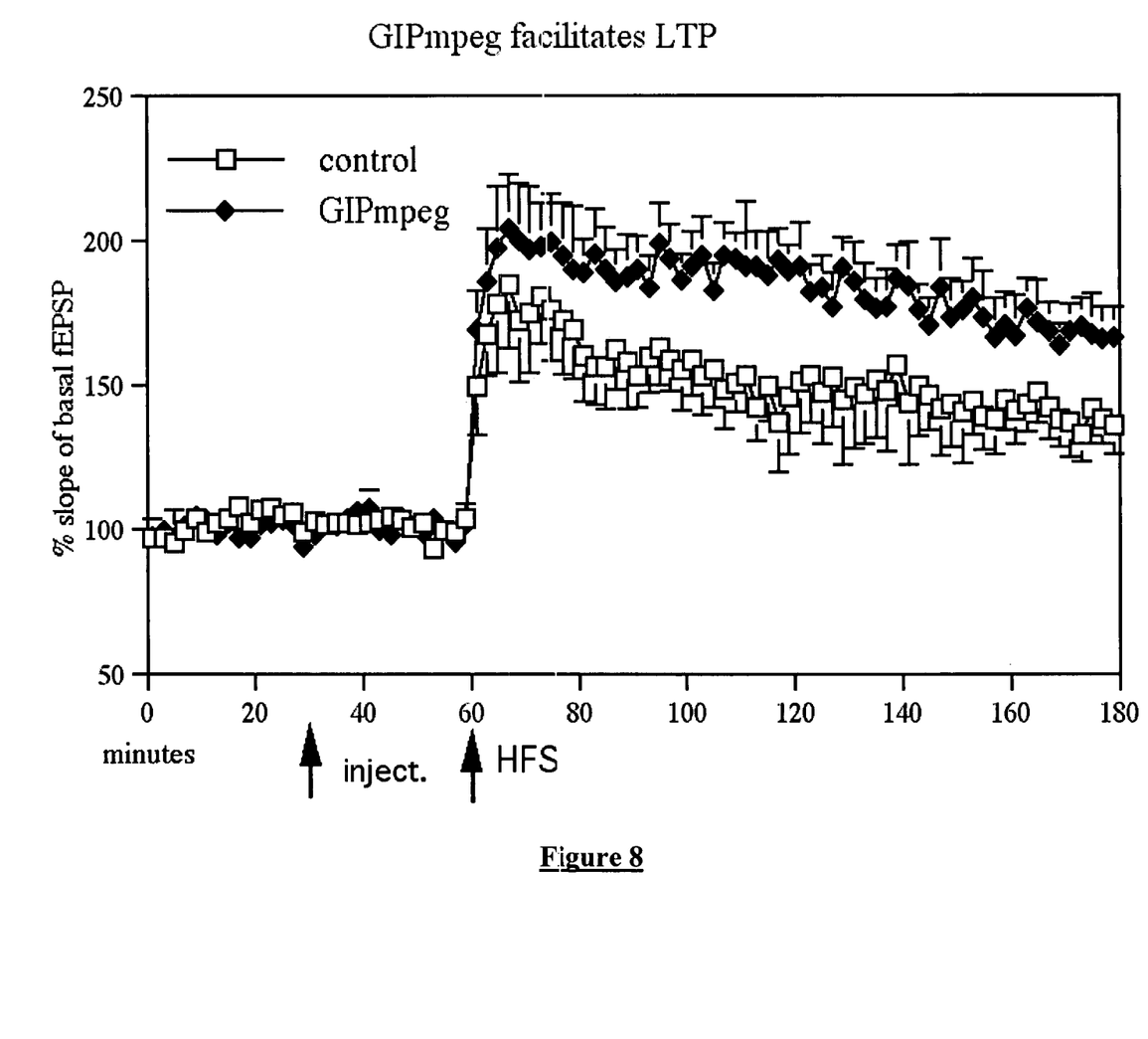
FIG. 8 illustrates the effect of [mPEG]GIP on long-term potentiation of synaptic transmission.

Male Wistar rats were icv injected with either vehicle (Control,) or 15 nmol GIP[mPEG], an analogue created by C-terminal mini-PEGylation of GIP (♦), where GIP[mPEG] is human GIP(1-42) having an attached polymer moiety of the general formula HO—(CH$_2$—O—CH$_2$)$_n$—H, in which n is about 3. LTP was induced 30 min post-injection using the HFS (weak protocol), and the change in EPSP assessed and graphed to represent the change in LTP. Injection (icv) of 15 nmol GIP[mPEG] enhanced long-term potentiation (LTP) compared with control. A two-way repeated measures ANOVA showed a difference between the GIP[mPEG] group and control ($p<0.001$). All groups n=6.

These results show that GIP[mPEG] has direct and acute modulating effects on synaptic transmission and can enhance the induction of LTP.

Example 9

In Vivo Effects of Treatment with the Stable GIP Agonist, GIP[Lys(37)Myristic Acid]

Figure 9:
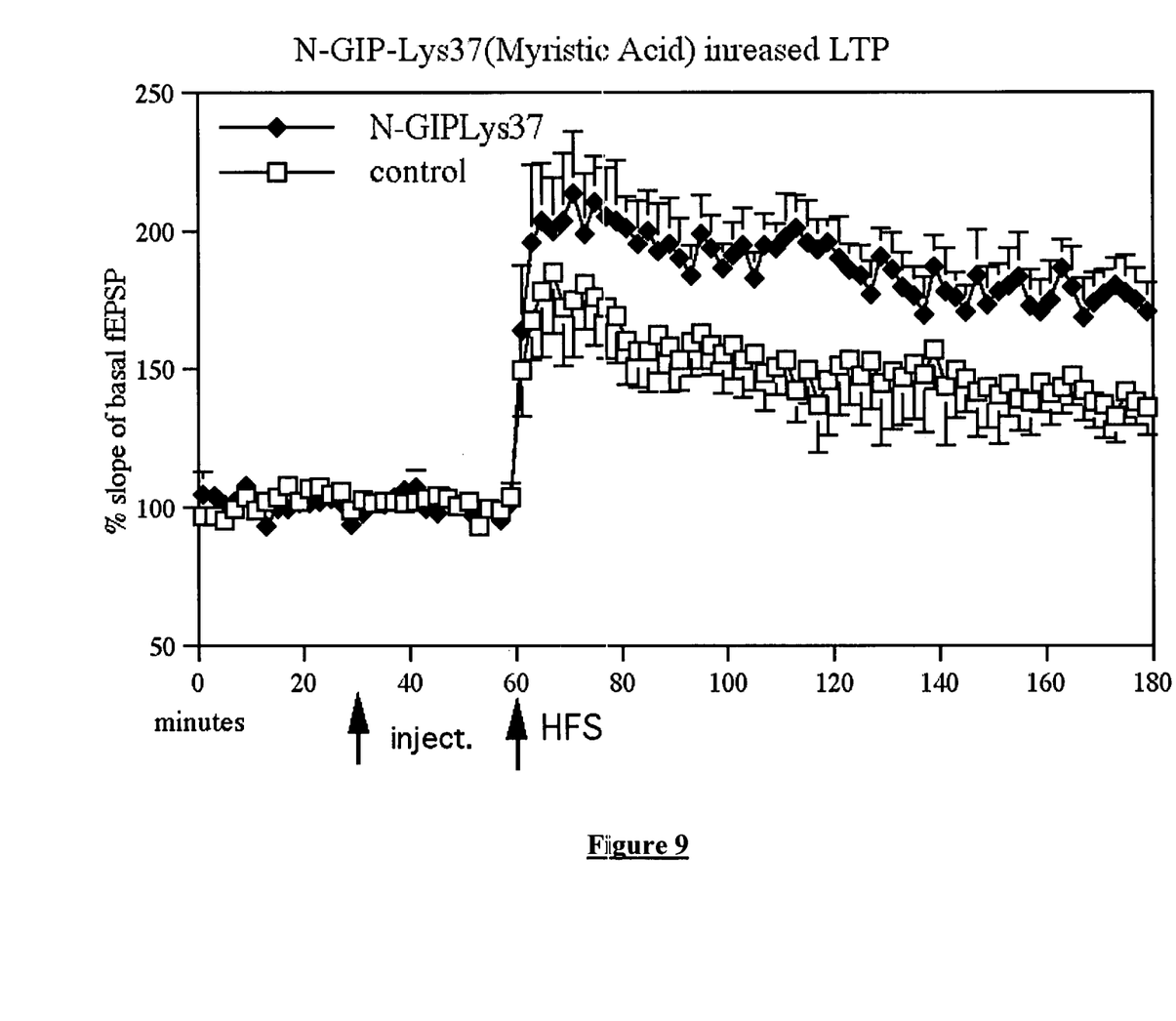
FIG. 9 illustrates the effect of Lys$^{37}$[Myristic acid]GIP on long-term potentiation of synaptic transmission.

Male Wistar rats were icv injected with either vehicle (Control,) or 15 nmol GIP[Lys(37)Myristic acid], an analogue created by modification by Myristic acid addition at an epsilon amino group of Lys(37) (♦). LTP was induced 30 min post-injection using the HFS (weak protocol), and the change in EPSP assessed and graphed to represent the change in LTP. Injection (icv) of 15 nmol GIP[Lys(37)Myristic acid] enhanced long-term potentiation (LTP) compared with control. A two-way repeated measures ANOVA showed a difference between the GIP[Lys(37)Myristic acid] group and control ($p<0.001$). All groups n=6.

These results show that GIP[Lys(37)Myristic acid] has direct and acute modulating effects on synaptic transmission and can enhance the induction of LTP.

Example 10

In Vivo Effects of Treatment with D-Ala(2)GIP Agonist

Figure 10:
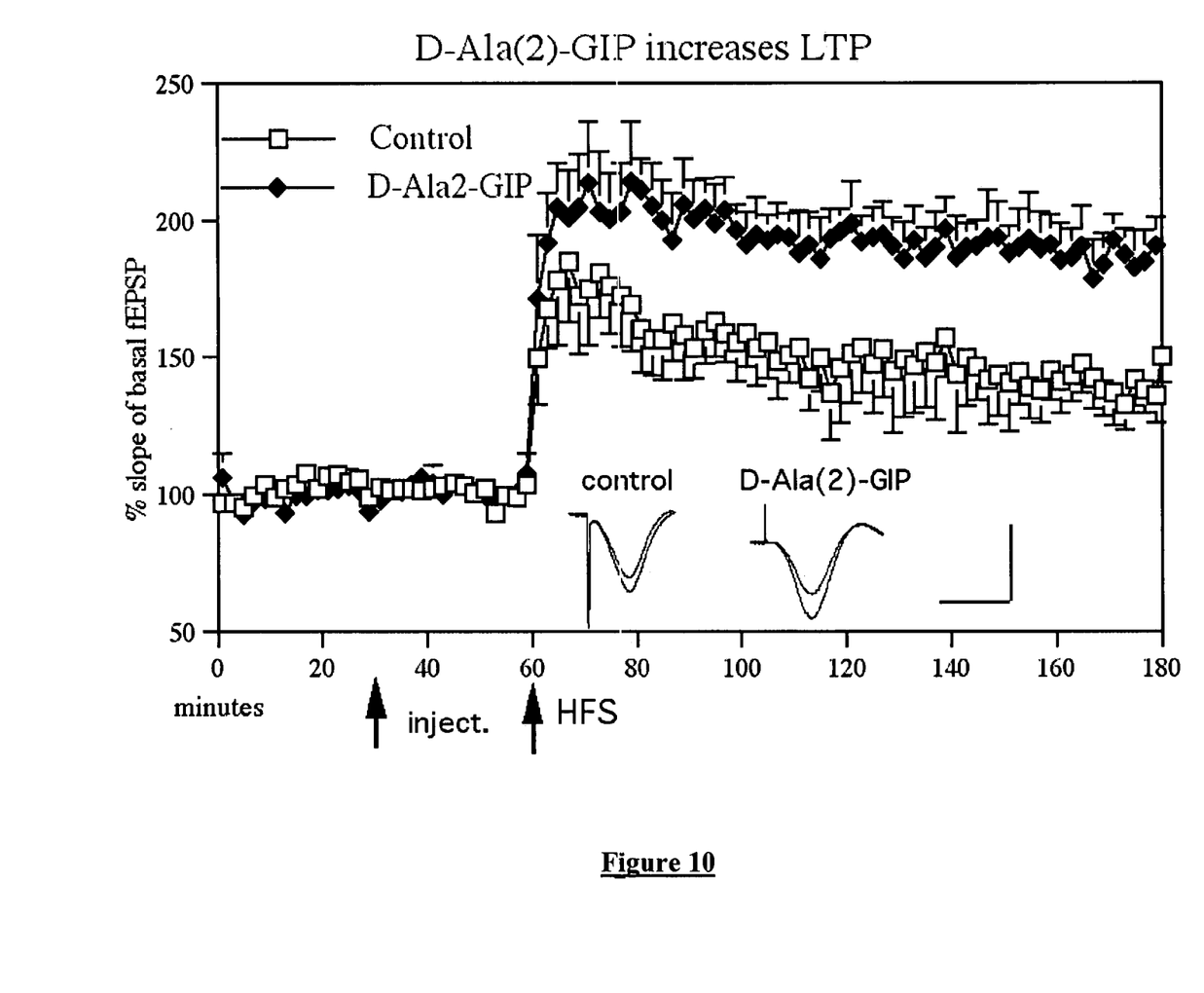
FIG. 10 illustrates the effect of D-Ala(2)GIP on long-term potentiation of synaptic transmission.

Male Wistar rats were icv injected with either vehicle (Control,) or 15 nmol D-Ala(2)GIP (♦). D-Ala(2)GIP is human GIP(1-42) in which L-Ala at position 2 has been replaced with D-Ala. LTP was induced 30 min post-injection using the HFS (weak protocol), and the change in EPSP assessed and graphed to represent the change in LTP. Injection (icv) of 15 nmol D-Ala(2)GIP enhanced long-term potentiation (LTP) compared with control. A two-way repeated measures ANOVA showed a difference between the D-Ala(2)GIP group and control ($p<0.001$). All groups n=6.

Averaged EPSPs are shown recorded 5 min pre-tetanus and 1 h post-tetanus. Calibration bars are 10 ms horizontal, 1 mV vertical.

These results show that D-Ala(2)GIP has direct and acute modulating effects on synaptic transmission and can enhance the induction of LTP.

Taken together, the results of the present study also show that the facilitating effects of GIP, and its agonist analogues, on synaptic plasticity can prevent the detrimental effects that βA(25-35) fragments have on LTP. It appears that the activation of GIP receptors triggers mechanisms that prime synapses for increased LTP and prevent or counteract the effects that beta-amyloid has on synaptic plasticity. Several mechanisms could be responsible for this. Without being bound by theory, we postulate that GIP, and its agonist analogues, act by altering voltage-dependent calcium channel (VDCC) and other ion channel activity. We furthermore suggest that the modulation of cAMP levels in neurons by GIP plays a role in the increase of neurotransmitter release, which then results in an enhancement of LTP. GIP, and its agonist analogues, might elevate cAMP levels in neurons in a similar way that it increases cAMP levels in pancreatic beta cells (Green et al., 2004). It has been shown that cAMP levels control the release of neurotransmitter vesicles in neurons. The GIP induced cAMP increase perhaps can enhance vesicle release in this fashion and make synaptic activity less dependent on VDCC activity, which is affected by beta-amyloid (Freir and Herron, 2003). VDCC activity would ordinarily be required to enhance cAMP levels via $Ca^{2+}$ sensitive nucleotide cyclases, and this step could be circumvented by the GIP/agonist analogues action. Since the chronically increased activation of $Ca^{2+}$ channels leads to neurotoxic processes such as the increased production of free radicals (Hölscher, 2005, 1998), the observation that GIP receptor activation prevents the effects of beta-amyloid holds great promise that the early degenerative effects of beta-amyloid can be reduced, and the downstream processes that lead to neurodegeneration can be prevented. In addition, the growth factor-like effects that GIP has on neurons by increasing stem cell proliferation and neuronal regeneration could help prevent or reduce long-term damage induced by beta-amyloid activity and plaque-induced gliosis (Perry and Greig, 2005; Perry et al., 2003).

In conclusion, these properties of GIP, and its agonistic peptide analogues, suggest that the treatment of subjects with stable GIP agonists could be an effective prophylactic treatment of neurological disorders caused by, or associated with, impaired LTP. Furthermore, the use of stable antagonistic peptides of GIP may be an attractive therapeutic agent in the treatment of hyperexcitability-type neurological disorders, wherein LTP is needed to be limited or reduced.

The invention claimed is:

1. A method of improving memory in a subject comprising administering to the subject a pharmaceutically acceptable amount of a GIP peptide analogue selected from the group consisting of:
   a peptide 12 to 42 amino acids in length and comprising at least 12 consecutive amino acid residues from the N-terminal end of gastric inhibitory polypeptide (SEQ ID NO:1);
   an analogue thereof 12 to 42 amino acids in length and comprising at least 12 consecutive amino acid residues from the N-terminal end of gastric inhibitory polypeptide (SEQ ID NO:1) with an amino acid substitution or modification consisting of
   acetylation at position 1;
   an analogue thereof 12 to 42 amino acids in length and comprising at least 12 consecutive amino acid residues from the N-terminal end of gastric inhibitory polypeptide (SEQ ID NO:1) with an amino acid substitution at position 2;
   an analogue thereof 12 to 42 amino acids in length and comprising at least 12 consecutive amino acid residues from the N-terminal end of gastric inhibitory polypeptide (SEQ ID NO:1) with a modification comprising the attachment of a polymer moiety of the general formula $HO-(CH_2-O-CH_2)_n-H$, in which n is an integer between 1 and about 22, to the alpha or epsilon amino groups of a lysine residue chosen from the group consisting of Lys(16), Lys(30), Lys(32), Lys(33), and Lys(37); and
   an analogue thereof 12 to 42 amino acids in length and comprising at least 12 consecutive amino acid residues from the N-terminal end of gastric inhibitory polypeptide (SEQ ID NO:1) with a modification by a fatty acid addition at an epsilon amino group of at least one lysine residue selected from Lys(16), Lys(30), Lys(32), Lys(33) and Lys(37).

2. A method according to claim 1, wherein the peptide analogue comprises acetylation at position 1.

3. A method according to claim 1, wherein the fatty acid is a C-14 myristoyl group added at an epsilon amino group of lysine residue Lys(37).

4. A method according to claim 1, wherein the peptide analogue comprises an amino acid substitution at position 2 by D-alanine.

5. A method according to claim 1, wherein said subject is suffering from Alzheimer's disease (AD).

* * * * *

SEQUENCE LISTING

```
<160> NUMBER OF SEQ ID NOS: 4

<210> SEQ ID NO 1
<211> LENGTH: 42
<212> TYPE: PRT
<213> ORGANISM: Homo sapiens

<400> SEQUENCE: 1

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 2
<211> LENGTH: 42
<212> TYPE: PRT
<213> ORGANISM: Artificial sequence
<220> FEATURE:
<223> OTHER INFORMATION: Synthetic analogue derived from human GIP(1-42)

<400> SEQUENCE: 2

Tyr Ala Pro Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 3
<211> LENGTH: 42
<212> TYPE: PRT
<213> ORGANISM: Artificial sequence
<220> FEATURE:
<223> OTHER INFORMATION: Synthetic analogue derived from human GIP(1-42)

<400> SEQUENCE: 3
```

```
Ala Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 4
<211> LENGTH: 42
<212> TYPE: PRT
<213> ORGANISM: Artificial sequence
<220> FEATURE:
<223> OTHER INFORMATION: Synthetic analogue derived from human GIP(1-42)

<400> SEQUENCE: 4

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40
```